(12) United States Patent
Choi et al.

(10) Patent No.: US 10,849,502 B2
(45) Date of Patent: Dec. 1, 2020

(54) SYSTEM AND METHOD FOR PROVIDING HEALTH DATA OF PERIPHERAL DEVICE

(71) Applicant: SAMSUNG ELECTRONICS CO., LTD., Suwon-si (KR)

(72) Inventors: Byung-hun Choi, Suwon-si (KR); Do-yoon Kim, Seongnam-si (KR); In-young Lee, Seoul (KR); Jae-geol Cho, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 527 days.

(21) Appl. No.: 14/618,290

(22) Filed: Feb. 10, 2015

(65) Prior Publication Data

US 2015/0223691 A1    Aug. 13, 2015

Related U.S. Application Data

(60) Provisional application No. 61/937,751, filed on Feb. 10, 2014.

(30) Foreign Application Priority Data

Aug. 20, 2014   (KR) ........................ 10-2014-0108450

(51) Int. Cl.
*A61B 5/00* (2006.01)
*G06F 19/00* (2018.01)

(52) U.S. Cl.
CPC .......... *A61B 5/0015* (2013.01); *A61B 5/0006* (2013.01); *A61B 5/0008* (2013.01); *G06F 19/3418* (2013.01)

(58) Field of Classification Search
None
See application file for complete search history.

(56) References Cited

U.S. PATENT DOCUMENTS

| 2007/0055738 | A1* | 3/2007 | Nakamoto | A61B 5/0002 709/217 |
| 2009/0193267 | A1* | 7/2009 | Chung | H04L 9/0836 713/193 |
| 2010/0235552 | A1 | 9/2010 | Holden et al. | |

FOREIGN PATENT DOCUMENTS

| KR | 1020060057534 A | 5/2006 |
| KR | 1020130051911 A | 5/2013 |

OTHER PUBLICATIONS

Communication dated Jul. 22, 2020 from the Korean Intellectual Property Office in application No. 10-2014-0108450.

* cited by examiner

*Primary Examiner* — Curtis A Kuntz
*Assistant Examiner* — Shawna M Kingston
(74) *Attorney, Agent, or Firm* — Sughrue Mion, PLLC

(57) ABSTRACT

A peripheral device for providing a health information message to a host device includes a health data obtainer configured to obtain health data; a message generator configured to determine a type of the health data, a private message identification (ID) corresponding to the type of the health data, and an ID of the peripheral device, and generate the health information message to include the private message ID, the ID of the peripheral device, and the health data; and a message provider configured to transmit the health information message to the host device, the private message ID being configured to be interpreted differently according to the ID of the peripheral device.

24 Claims, 7 Drawing Sheets

<Standard Message Format>

| Byte | Attribute | Length |
|---|---|---|
| 1 | Message Type(0x00) — 402 | 1 Byte |
| 2 | Message Flag — 404<br>Bit 7: Confirmed(1) or Unconfirmed(0)<br>Bit 6: Set Action(1) or Normal(0)<br>Bit 5~0: Reserved | 1 Byte |
| 3 | Invoke ID — 406 | 1 Byte |
| 4 | Extended Message ID — 408 | 1 Byte |
| 5 | Length(n-5) — 410 | 4 Bytes |
| 9~n | Message Body — 412 | n-8 |

< Extended Message Format >

SYSTEM AND METHOD FOR PROVIDING HEALTH DATA OF PERIPHERAL DEVICE

CROSS-REFERENCE TO RELATED APPLICATIONS

This application claims priority to U.S. Provisional Application No. 61/937,751, filed on Feb. 10, 2014, in the U.S. Patent and Trademark Office and Korean Patent Application No. 10-2014-0108450, filed on Aug. 20, 2014, in the Korean Intellectual Property Office, the disclosures of which are incorporated herein in their entireties by reference.

BACKGROUND

1. Field

One or more exemplary embodiments relate to a system and method for providing health data of a peripheral device, which are capable of identifying a health information message based on a private message identification (ID).

2. Description of the Related Art

Recently, for the health, fitness and wellness of users, various health care devices have been put on the market. By connecting a health care device to a host device, a user can use complex health care services.

A health care device is a peripheral device of a host device and may be connected to the host device. The host device may control and manage the health care device by using an application. Thus, there is a growing need to develop a data transmission protocol for sharing data between the health care device and the host device.

There are the Continua (IEEE 11073-20601) protocol and the ANT+ protocol as transmission standards for sharing data measured by various types of health care devices. However, there are many situational and functional limits in applying the Continua protocol and the ANT+ protocol. For example, although the Continua protocol is applicable to health care devices for general purposes, only measurement results can be transmitted using the Continua protocol, and device control cannot be performed using the Continua protocol. When the ANT+ protocol is used, only an ANT, which is a communication module, is used and raw data such as electrocardiogram (ECG) data or plethysmogram data cannot be transmitted in real time. Also, device control cannot be performed when the ANT+ protocol is used, similar to the Continua protocol.

Also, in order to apply the Continua protocol and the ANT+ protocol to a new health care device, data should be added or modified. However, adding or modifying data takes a large amount of time. Thus, the Continua protocol and the ANT+ protocol are difficult to flexibly apply to various health care devices.

Accordingly, there is a need for a technique of effectively identifying and interpreting health information messages generated by various types of health care devices, based on a limited number of message identifications (IDs).

SUMMARY

One or more exemplary embodiments may provide a health data providing system and method capable of generating and providing a health information message including health data and a private message identification (ID).

One or more exemplary embodiments may further provide a health data providing system and method capable of interpreting a health information message, based on a private message ID and an ID of a peripheral device.

One or more exemplary embodiments may further provide a health data providing system and method capable of providing health data generated by sub-peripheral devices connected to a peripheral device to a device from the peripheral device.

Additional aspects will be set forth in part in the description which follows and, in part, will be apparent from the description, or may be learned by practice of the presented exemplary embodiments.

According to an aspect of one or more exemplary embodiments, there is provided a peripheral device for providing a health information message to a host device including a health data obtainer configured to obtain health data; a message generator configured to determine a type of the health data, a private message identification (ID) corresponding to the type of the health data, and an ID of the peripheral device, and generate the health information message to include the private message ID, the ID of the peripheral device, and the health data; and a message provider configured to transmit the health information message to the host device, wherein the private message ID is configured to be interpreted differently according to the ID of the peripheral device.

The message generator may be further configured to generate a message ID of the health information message, and the message ID may be classified as one of the private message ID and a common message ID.

The message ID may be expressed in a predetermined number of bits. Some values expressed in the predetermined number of bits may indicate the private message ID. Other values expressed in the predetermined number of bits may indicate the common message ID.

The health data may include raw data, and the peripheral device may further include a sensor configured to measure the raw data.

The health data obtainer may be configured to obtain health data generated by sub-peripheral devices connected to the peripheral device, and the message generator may be configured to generate a health information message to include the health data generated by the sub-peripheral devices and IDs of the sub-peripheral devices.

The health information message including the health data generated by the sub-peripheral devices and the ID of the sub-peripheral device may include the private message ID. The health data generated by the sub-peripheral devices may be configured to be extracted by the host device, based on the private message ID and the IDs of the sub-peripheral devices.

The peripheral device may further include a message receiver configured to receive a request for additional health data from the host device. The message generator may be configured to generate a health information message to include the health data generated by the sub-peripheral devices and the IDs of the sub-peripheral devices, in response to the request for the additional health data.

The peripheral device may be configured to transmit a list of the sub-peripheral devices and a list of the health data generated by the sub-peripheral devices to the host device, in response to the request for the additional health data.

The sub-peripheral devices may be included in the peripheral device.

The health information message may include a standard message format or an extended message format.

According to another aspect of an exemplary embodiment, a method of providing a health information message from a peripheral device to a host device includes obtaining health data; determining a type of the health data, a private message identification (ID) corresponding to the type of the health data, and an ID of the peripheral device; generating the health information message to include the private message ID, the ID of the peripheral device, and the health data; and transmitting the health information message to the host device, wherein the private message is configured to be interpreted differently according to the ID of the peripheral device.

The method may further include classifying a message ID of the health information message as one of the private message ID and a common message ID.

The message ID may be expressed in a predetermined number of bits. Some values expressed in the predetermined number of bits may indicate the private message ID. Other values expressed in the predetermined number of bits indicate the common message ID.

The health data may include raw data, and the method may further include measuring the raw data in real time by using a sensor of the peripheral device.

The obtaining may include obtaining health data generated by sub-peripheral devices connected to the peripheral device. The generating of the health information message may include generating the health information message to include the health data generated by the sub-peripheral devices and IDs of the sub-peripheral device.

The health information message including the health data generated by the sub-peripheral devices and the IDs of the sub-peripheral devices may include the private message ID, and the health data generated by the sub-peripheral devices may be configured to be extracted by the host device, based on the private message ID and the IDs of the sub-peripheral devices.

The method may further include receiving a request for additional health data from the host device, and the generating of the health information message may include generating the health information message to include the health data generated by the sub-peripheral devices and the IDs of the sub-peripheral devices, in response to the request for the additional health data.

The method may further include transmitting a list of the sub-peripheral devices and a list of the health data generated by the sub-peripheral devices to the host device, in response to the request for the additional health data.

The sub-peripheral devices may be included in the peripheral device.

The health information message may include a standard message format or an extended message format.

According to another aspect of one or more exemplary embodiments, there is provided a non-transitory computer-readable recording medium having recorded thereon at least one program including commands which, when executed, cause a computer to perform a method of providing a health information message from a peripheral device to a host device, the method including obtaining health data; determining a type of the health data, a private message identification (ID) corresponding to the type of the health data, and an ID of the peripheral device; generating the health information message to include the private message ID, the ID of the peripheral device, and the health data; and transmitting the health information message to the host device, wherein the private message ID is configured to be interpreted differently according to the ID of the peripheral device.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1:
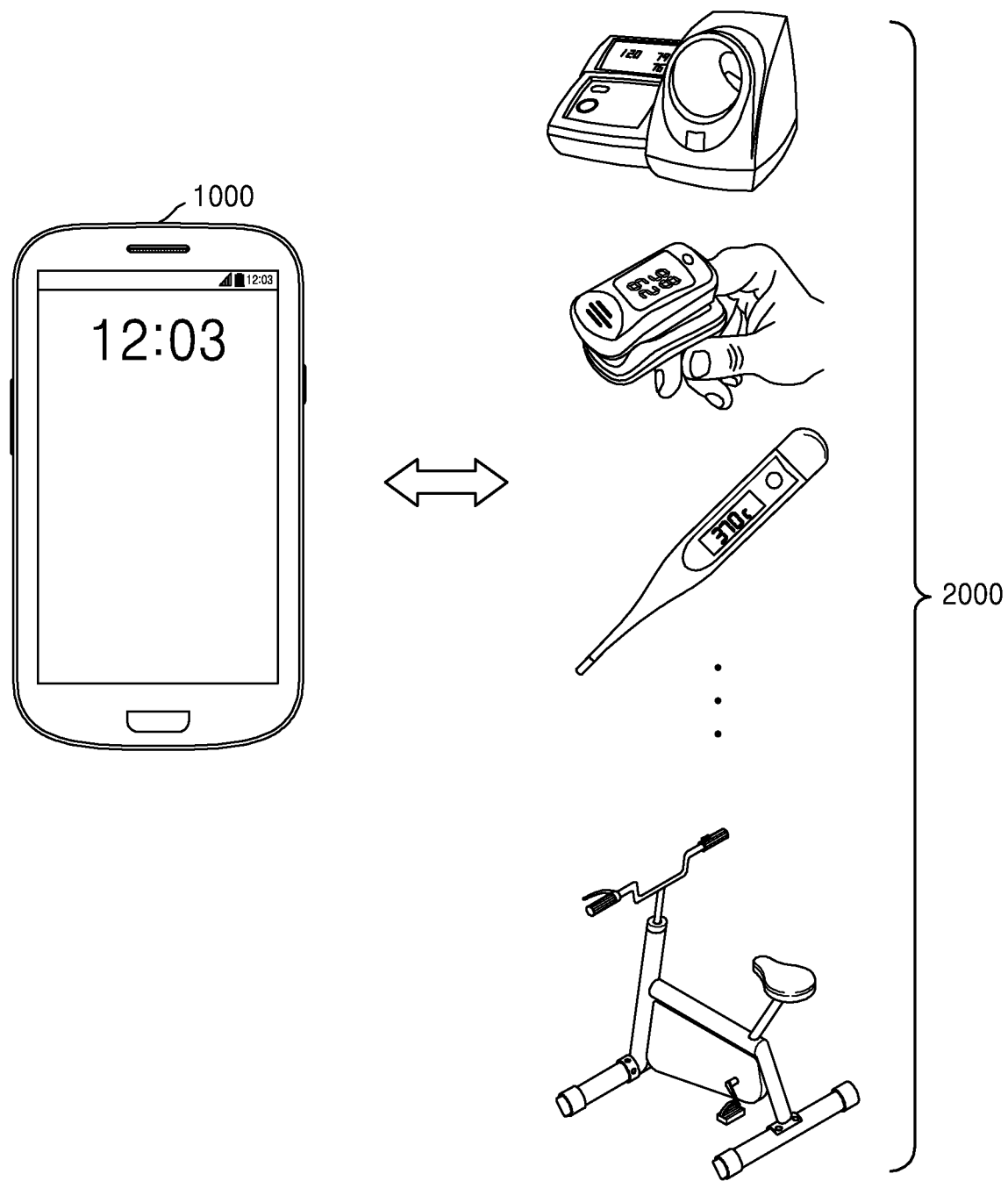
FIG. 1 is a diagram illustrating a health data providing system in which health data is transmitted between a host device and a peripheral device, according to an exemplary embodiment.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects of the present description. For clarity, parts of the exemplary embodiments that are not related to explaining the exemplary embodiments are omitted in the drawings. As used herein, the term "and/or" includes any and all combinations of one or more of the associated listed items.

In the present disclosure, it is understood that when an element or layer is referred to as being "connected" to another element or layer, the element or layer can be directly connected to another element or layer or can be electrically connected to another element or layer with intervening elements or layers therebetween. It is further understood that the terms "comprise" and/or "comprising," when used in this specification, specify the presence of stated features, integers, steps, operations, elements, and/or components, but do not preclude the presence or addition of one or more other features, integers, steps, operations, elements, components, and/or groups thereof.

Also, in the present disclosure, a standard message format may be understood as a message format having a fixed length, and an extended message format may be understood as a message format having an extendable length. The standard message format may be a basic message format and may be used to transmit most messages. The extended message format may be used to transmit messages including a large amount of information, e.g., raw data.

A message identification (ID) may be a value for identifying a message. Data and a message contained in a message body may be identified by, for example, a host device 1000 or a peripheral device 2000 illustrated in FIG. 1, based on the message ID. Message IDs may be classified into common message IDs and private message IDs. For example, a message ID may be a value that is 1 byte long.

In the present disclosure, a common message ID may refer to a message ID that is commonly applied to the host device 1000 and the peripheral device 2000. Messages assigned the same common message ID may be the same type of messages regardless of the host device 1000 and the peripheral device 2000. For example, when a message ID is expressed in a 1-byte value, a common message ID may have a value of "0x00" to "0x4F".

Private message IDs may be IDs that identify messages that are specialized for the host device 1000 and the peripheral device 2000. Since a private message ID may correspond to the ID of the host device 1000 or the ID of the peripheral device 2000, the private message ID may be used to identify the message that is specialized for the host device 1000 or the peripheral device 2000. For example, when a message ID is expressed in a 1-byte value, a private message ID may have a value of "0x50" to "0x9F".

Raw data may be data measured and generated by the peripheral device 2000, and may include, for example, generic waveform data, electrocardiogram data, electroencephalogram data, electrooculogram data, electromyogram data, blood pressure data, data regarding a galvanic skin response (GSR), plethysmogram data, blood flow data, and body temperature data.

Also, additional health data is health data generated by a sub-peripheral device connected to the peripheral device 2000 and provided from the peripheral device 2000 to the host device 1000.

Hereinafter, exemplary embodiments will be described in detail with reference to the accompanying drawings.

FIG. 1 is a diagram illustrating a health data providing system for transmitting health data between the host device 1000 and at least one peripheral device 2000, according to an exemplary embodiment.

Referring to FIG. 1, the host device 1000 is connected to the at least one peripheral device 2000, and may exchange a health information message with the at least one peripheral device 2000. The health information message may be a message for exchanging health data generated by the at least one peripheral device 2000 between the at least one peripheral device 2000 and the host device 1000. The at least one peripheral device 2000 may generate the health data by measuring a user's health state or the state of the at least one peripheral device 2000 itself by using, for example, a sensor (not shown) included therein. The health information message may include, for example, a message requesting the health data and a message including the health data, but is not limited thereto.

Examples of a format of the health information message may include a standard message format and an extended message format. The host device 1000 and the at least one peripheral device 2000 may selectively generate a health information message in the standard message format or the extended message format, based on the type of the health data to be included in a message.

The health information message exchanged between the host device 1000 and the at least one peripheral device 2000 may have a common message ID and a private message ID. The private ID of the host device 1000 and the ID of the host device 1000 may be used in combination and the private ID of the at least one peripheral device 2000 and the ID of the at least one peripheral device 2000 may be used in combination. Thus, the host device 1000 and the at least one peripheral device 2000 may efficiently use a limited number of bit values to identify the health information message.

In order to provide health data generated by sub-peripheral devices 2010 and 2020 (see FIGS. 9A and 9B) of the at least one peripheral device 2000 to the host device 1000, the at least one peripheral device 2000 may generate a health information message including the health data of the respective sub-peripheral devices 2010 and 2020. Also, in order to identify the health data of the respective sub-peripheral devices 2010 and 2020, the at least one peripheral device 2000 may include the private message ID of the at least one peripheral device 2000 and respective IDs of the sub-peripheral devices 2010 and 2020 into the health information message. In this case, the sub-peripheral devices 2010 and 2020 may be connected to or included in the at least one peripheral device 2000.

The host device 1000 may be a device that uses and manages the health data generated by the peripheral device 2000. For example, the host device 1000 may be, but is not limited to, a smartphone, a smart TV, a mobile phone, a personal digital assistant (PDA), a laptop computer, a media player, a micro-server, a global positioning system (GPS) device, an electronic book terminal, a digital broadcasting terminal, a navigation device, a kiosk, an MP3 player, a digital camera, and another mobile/non-mobile computing device.

The at least one peripheral device 2000 is a device that may generate health data and be connected to the host device 1000 via a wired/wireless network. Examples of the at least one peripheral device 2000 may include devices including a pulse oximeter, a blood pressure monitor, a heart rate monitor, a body composition analyzer, an apparatus to monitor fitness, a glucose meter, an insulin data logger, a medication monitor, a thermometer, a peak expiratory flow meter, an actigraph, a scale to measure weight, a speed and distance monitor, and an apparatus configured to be used with a bicycle.

Figure 2:
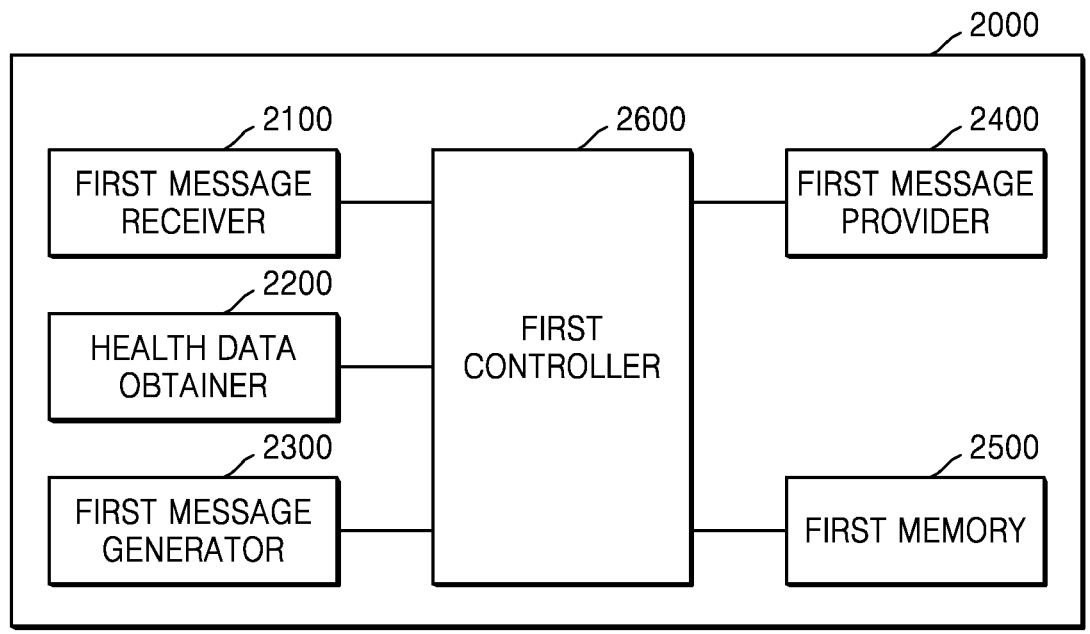
FIG. 2 is a block diagram of a peripheral device according to an exemplary embodiment.

FIG. 2 is a block diagram of a peripheral device 2000 according to an exemplary embodiment.

Referring to FIG. 2, the peripheral device 2000 according to an exemplary embodiment includes a message receiving unit 2100 (e.g., first message receiver), a health data obtaining unit 2200 (e.g., health data obtainer), a message generating unit 2300 (e.g., first message generator), a message providing unit 2400 (e.g., first message provider), a first memory 2500, and a control unit 2600 (e.g., first controller).

The message receiving unit 2100 may receive a request for health data from the host device 1000. Examples of the health data requested by the host device 1000 may include raw data generated by the peripheral device 2000 and information regarding a format of the raw data, but are not limited thereto.

Also, the message receiving unit 2100 may receive a request for a list of additional health data from the host device 1000. The additional health data may be health data generated by the sub-peripheral devices 2010 and 2020 of FIGS. 9A and 9B. The sub-peripheral devices 2010 and 2020 may be connected to or included in the peripheral device

2000. Also, the message receiving unit 2100 may receive a request for the additional health data from the host device 1000.

The health data obtaining unit 2200 obtains health data. Examples of the health data obtaining unit 2200 may include a pulse oximeter, a blood pressure monitor, a heart rate monitor, a body composition analyzer, an apparatus configured to monitor fitness, a glucose meter, an insulin data logger, a medication monitor, a thermometer, a peak expiratory flow meter, an actigraph, a scale configured to measure weight, a speed and distance monitor, and an apparatus configured to be used with a bicycle. The health data may be measured by a sensor included in the peripheral device 2000 and obtained by the health data obtaining unit 2200. Also, the health data may be raw data measured by the peripheral device 2000.

Also, the health data obtaining unit 2200 may receive health data generated by the sub-peripheral devices 2010 and 2020 from the sub-peripheral devices 2010 and 2020. In this case, the sub-peripheral devices 2010 and 2020 may be external devices connected to the peripheral device 2000 or may be devices included in the peripheral device 2000.

The message generating unit 2300 generates a health information message to be provided to the host device 1000. The message generating unit 2300 may generate the health information message in response to a request from the host device 1000. However, exemplary embodiments are not limited thereto, and the message generating unit 2300 may generate the health information message to be provided to the host device 1000 regardless of whether a request from the host device 1000 is received. For example, the message generating unit 2300 may generate the health information message to provide the alarm information to the host device 1000 even if a request for the health information message is not received from the host device 1000.

Also, the message generating unit 2300 may determine whether the health information message is to be generated in a standard message format or an extended message format, based on the type of health data to be provided to the host device 1000.

In this case, the health information message may be classified into a health information message in a standard message format and a health information message in an extended message format. The health information message in the standard message format may be used to transmit health data generated by the peripheral device 2000 and device information regarding the peripheral device 2000 in the standard message format. When the health data is variably generated by the peripheral device 2000 according to, for example, preset times that the health data is to be generated or a preset number of times that the health data is to be generated, it may be difficult transmit the health data in a message in the standard message format. Accordingly, the health information message in the extended message format may be exchanged between the host device 1000 and the peripheral device 2000. For example, the health information message in the extended message format may be used when the types of bio-signal data measured in real time by the peripheral device 200 are greater than a predetermined level or when health data measured by a plurality of peripheral devices 200 is transmitted together. The health information message in the extended message format may have a variable length. For example, when the size of a message of measured bio-signal data is large, the health information message in the extended message format may be used to transmit the measured bio-signal data.

A header of the health information message may include a message ID that identifies information included in the health information message. For example, the health information message in the standard message format may include a 4-byte header, and a value of 1 byte of the 4 bytes may represent a message ID that identifies the health information message. Also, for example, the health information message in the extended message format may include an 8-byte header, and a value of 1 byte of the 8 bytes may represent a message ID that identifies the health information message. The standard message format and the extended message format will be described in more detail with reference to FIGS. 3 and 4 below.

A message ID that identifies a health information message may be classified as one of a common message ID and a private message ID. In detail, a message ID included in a health information message in the standard message format may be classified as one of a common message ID and a private message ID. A message ID included in a health information message in the extended message format may be also classified as one of a common message ID and a private message ID.

The common message ID may be a message ID to be commonly applied to the host device 1000 and the peripheral device 2000. Messages assigned the same common message ID may be the same type of messages regardless of the host device 1000 and the peripheral device 2000. Also, a message identified using the common message ID may not be specifically configured for the host device 1000 or the peripheral device 2000. Examples of a message that may be identified using the common message ID may include the following:

data request message: a message for requesting the peripheral device 2000 to provide data;

product information message: a message for providing product information of the peripheral device 2000;

extended product information message: a message for providing product-extended information to the peripheral device 2000;

data & time message: a message for checking or setting date and time information of the peripheral device 2000;

setting message: a message for checking or changing settings of the peripheral device 2000;

device status message: a message for providing device status information related to a battery voltage and other performance indicators of the peripheral device 2000.

memory status message: a message for providing memory information of the peripheral device 2000 (e.g., a total memory space and an available memory space);

raw data format message: a message for providing information regarding a data format of a signal measured by the peripheral device 2000, e.g., a pulse plethysmogram or an electrocardiogram;

simple raw data format message: a message for changing channel information of raw data provided from the peripheral device 2000, sample size of the raw data, a sampling frequency, etc.;

real-time raw data request message: a message for requesting the peripheral device 2000 to provide generated raw data in real time;

raw data message: a message for providing the raw data generated by the peripheral device 2000, which may be included in a health information message in the extended message format;

alert message: a message used for the peripheral device 2000 to transmit a message that is not requested by the host device 1000, e.g., an alert or a notice, which may be included in a health information message in the extended message format;

extended alert message: an extended message of an alert message, which may include a character string;

user information message: a message for obtaining or setting user information;

response message: a message for responding to a message that the host device 1000 requests the peripheral device 2000 to provide;

event reporting message: a message for transmitting an event generated by the peripheral device 2000 to the host device 1000, which may be included in a health information message in the extended message format;

extended event report message: an extended message of an event reporting message, which may include a character string;

extra type list message: a message for providing a list of the sub-peripheral devices 2010 and 2020 connected to the peripheral device 2000 (For example, when the sub-peripheral devices 2010 and 2020, e.g., a blood pressure monitor, a thermometer, and a scale are included in the peripheral device 2000, the extra type list message may include the IDs of the blood pressure monitor, the thermometer, and the scale);

extra data message: a message for transmitting an extra type of data;

delete stored data message: a message for deleting records stored in the peripheral device 2000;

recording status message: a message representing a state of data (which is measured by the peripheral device 2000) stored in a memory of the peripheral device 2000;

start record message: a message for causing the peripheral device 2000 to individually start or end data recording; and change status message: a message for changing a state of the peripheral device 2000, which may be used to, for example, power off or initialize the peripheral device 2000.

A private message ID may be an ID that identifies a message that is specialized (e.g., specially configured) for the host device 1000 or the peripheral device 2000. Since the private message ID corresponds to the ID of the host device 1000 or the ID of the peripheral device 2000, the private message ID may be used to identify a message specialized for the host device 1000 or the peripheral device 2000. For example, when the private message ID has a value of '0x70' and the peripheral device 2000 is a pulse oximeter, the private message ID having the value of '0x70' may represent a message indicating a pulse rate measured by the pulse oximeter. As another example, when the private message ID has a value of '0x70' and the peripheral device 2000 is a scale, the private message ID having the value of '0x70' may represent a message indicating a weight measured by the scale.

Examples of a message that may be distinctively identified using a private message ID may include the following:

pulse oximeter message: a message related to an SpO2 value, a message related to a pulse rate, a message related to a plethysmogram, etc.;

blood pressure monitor message: a message related to maximum blood pressure, a message related to minimum blood pressure, a message related to average blood pressure, etc.;

heart rate monitor message: a message related to an electrocardiogram waveform, a message related to a measured heart rate, a message related to a recommended heart rate, a message related to an R-R interval, etc.;

body composition analyzer message: a message related to a weight, a message related to a height, a message related to a body fat percentage, a message related to total body water, a message relate to a BMI, a message related to muscle mass, etc.;

fitness apparatus message: a message related to selecting the type of fitness apparatus, a message related to measuring the amount of exercise, etc.;

glucose meter message: a message related to measuring blood sugar (before and after a meal), a message related to the amount of exercise, a message related to a measurement position, etc.;

insulin data logger message; a message related to an insulin infusion rate;

medication monitor message: a message related to pill bottle information; a message related to an alarm indicating a time for taking medication, etc.;

thermometer message: a message related to body temperature, a message related to a measurement position, etc.;

peak expiratory flow meter message: a message related to measuring lung capacity;

actigraph message: a message related to the amount of activity, a message related to an activity cycle, etc.;

scale message: a message related to a weight measured by the scale, a message related to a height of a user being weighted by the scale, etc.;

speed and distance monitor message: a message related to a distance, a message related to a speed, a message related to calorie consumption, a message related to a longitude, a message related to a latitude, etc.; and bicycle apparatus message: a message related to a force applied to bicycle pedals, a message related to a biking speed, a message related to cadence, etc.

A message that may be identified using a private message ID may include data included in at least two messages among the above messages. For example, when the peripheral device 2000 is a blood pressure monitor, a message that may be identified using a private message ID may be a message related to maximum blood pressure, minimum blood pressure, and average blood pressure. The message related to maximum blood pressure may include, but is not limited to, a message for measuring maximum blood pressure by using the peripheral device 2000 and a message indicating maximum blood pressure measured by the peripheral device 2000.

Also, the message generating unit 2300 may determine whether a health information message having a common message ID or a health information message having a private message ID is to be generated, based on the type of health data to be provided to the host device 1000. A message ID may be expressed in a predetermined number of bits, and some values expressed in the predetermined number of bits may be set to a private message ID and other values expressed in the predetermined number of bits may be set to a common message ID. For example, a message ID of a health information message may be expressed using a 1-byte value, a value of "0x00" to "0x4F" may represent a common message ID, and a value of "0x50" to "0x9F" may represent a private message ID.

When the message generating unit 2300 determines to generate a health information message having a private message ID, the message generating unit 2300 may determine an ID of the peripheral device 2000 and a private message ID corresponding to the type of health data. Also, the message generating unit 2300 may insert the ID of the peripheral device 2000 into the health information message. Thus, the host device 1000 may detect the ID of the peripheral device 2000 and the type of heath data that matches the private message ID, extract the health data from the health information message generated by the message generating unit 2300, and interpret the health data.

The message providing unit 2400 transmits the health information message to the host device 1000. The message providing unit 2400 may transmit the health information message to the host device 1000 in response to a request from the host device 1000. However, exemplary embodiments are not limited thereto, and the message providing unit 2400 may transmit the health information message to the host device 1000 even when a request for the health information message is not received from the host device 1000.

The memory 2500 stores data needed for the peripheral device 2000 to generate the health information message and provide the health information message to the host device 1000.

The control unit 2600 controls overall operations of the peripheral device 2000. The control unit 2600 may control the message receiving unit 2100, the health data obtaining unit 2200, the message generating unit 2300, the message providing unit 2400, and the memory 2500 in such a manner that the peripheral device 2000 may generate the health information message and provide the health information message to the host device 1000.

At least one of the message receiving unit 2100, the health data obtaining unit 2200, the message generating unit 2300, the message providing unit 2400, and the control unit 2600 may be operated using a software module, but are not limited thereto. Also, at least one of the message receiving unit 2100, the health data obtaining unit 2200, the message generating unit 2300, the message providing unit 2400, the memory 2500 and the control unit 2600 may be operated by hardware.

At least one of the message receiving unit 2100, the health data obtaining unit 2200, the message generating unit 2300, and the message providing unit 2400 may be included in the control unit 2600. At least one of the message receiving unit 2100, the health data obtaining unit 2200, the message generating unit 2300, the message providing unit 2400, and the control unit 2600 may be operated by or implemented as a processor. Exemplary embodiments are, however, not limited thereto.

Figure 3:
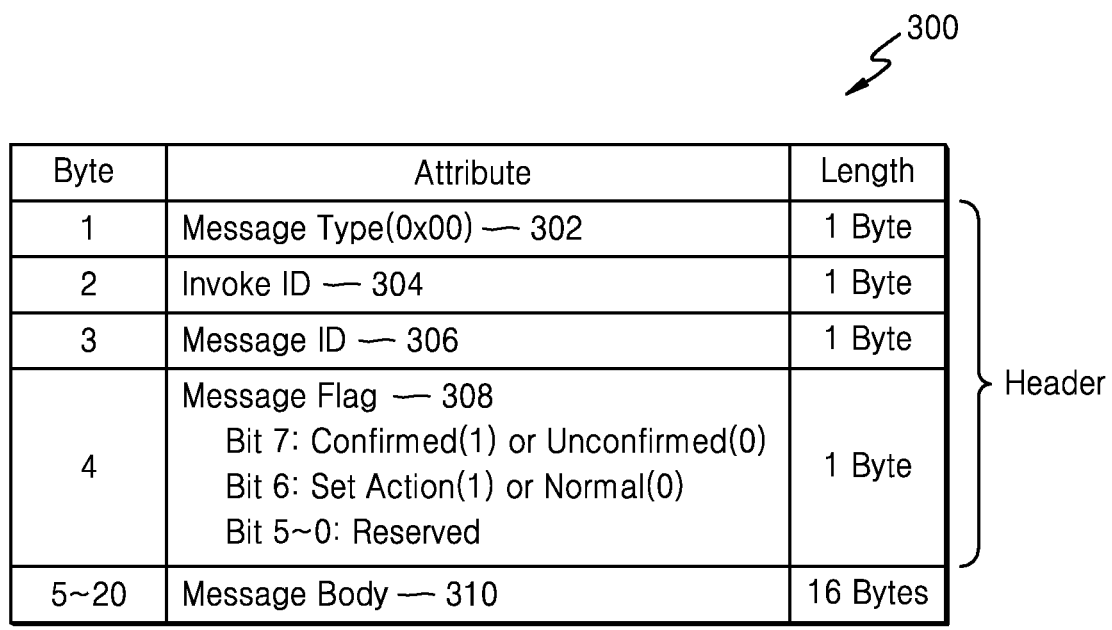
FIG. 3 is a table illustrating a standard message format according to an exemplary embodiment.

FIG. 3 is a table illustrating a standard message format according to an exemplary embodiment.

Referring to FIG. 3, a health information message 300 in a standard message format may consist of a total of 20 bytes. The health information message 300 in the standard message format may include a 4-byte message header and a 16-byte message body.

The message header may include a "message type" 302, an "invoke ID" 304, a "message ID" 306, and a "message flag" 308.

The "message type" 302 represents whether the health information message is in the standard message format or the extended message format. For example, the health information message is in the standard message format when the "message type" 302 has a value of "0x00" and in the extended message format when the "message type" 302 has a value of "0x10".

The "invoke ID" 304 may be a value representing a request for information when a host device 1000 requests a peripheral device 2000 to provide the information, as will be described with reference to FIG. 6 below. When the host device 1000 requests the peripheral device 2000 to provide the information, the "invoke ID" 304 may always be a value greater than '0'. Also, the peripheral device 2000 may respond to the request by using the 'invoke ID' 304 used to request the information.

Also, as will be described with reference to FIG. 6 below, the "invoke ID" 304 may be '0' when the peripheral device 2000 transmits a message to the host device 1000 when a request for the message is not received from the host device 1000.

The "message ID" 306 represents an ID of a message. The "message ID" 306 may be determined to be a common message ID when the "message ID" 306 is a value of "0x00 to 0x4F", and may be determined to be a private message ID when the "message ID" 306 is a value of "0x50 to 0x9F".

A health information message of a common message ID may be a message commonly applied to peripheral devices 2000. For example, a health information message having a message ID 306 of '0x00' (e.g., a data request message) may be interpreted to be the same message by all the peripheral devices 2000 and the host device 1000.

A health information message having a private message ID may be interpreted differently in units of peripheral devices 2000. For example, when a health information message having a message ID 306 of '0x70' is used in relation to a pulse oximeter, the health information message may be interpreted as a message representing a pulse rate measured by the pulse oximeter. As another example, when the health information message having the message ID 306 of '0x70' is used in relation to a scale, the health information message may be interpreted as a message representing a weight measured by the scale.

The host device 1000 may receive a result of processing a message from the peripheral device 2000 by setting a bit '7' of the "message flag" 308 to '1'. Also, the host device 1000 may set a bit '6' and transmit the message to change or control settings of the peripheral device 2000.

The "message body" 310 represents health data to be exchanged between the host device 1000 and the peripheral device 2000. The structure of the "message body" 310 may depend on the "message ID" 306. Received attributes may be present in "message body" regions of most messages.

Figures 4, 5:
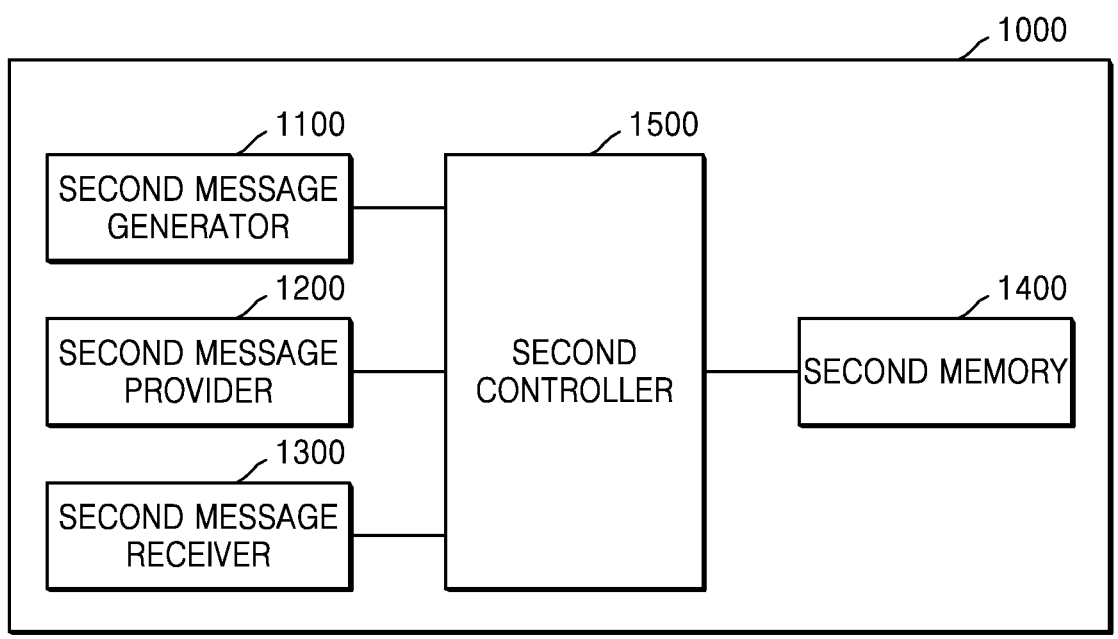
FIG. 4 is a table illustrating an extended message format according to an exemplary embodiment.
FIG. 5 is a block diagram of a host device according to an exemplary embodiment.

FIG. 4 is a table illustrating an extended message format according to an exemplary embodiment. The extended message format is a variable-length format and may be used to transmit a large amount of data. For example, a message in the extended message format may be used to transmit data, the amount of which is large and thus cannot be transmitted in a message in the standard message format, e.g., raw data.

Referring to FIG. 4, a health information message 400 in the extended message format may include an 8-byte message header and an extendable message body.

The message header may include a "message type" 402, a "message flag" 404, an "invoke ID" 406, an "extended message ID" 408, and a "length" 410.

The "message type" 402 represents whether the health information message is in the extended message format. For example, the health information message may be a message in the extended message format when the "message type" 402 has a value of "0x10".

The host device 1000 of FIG. 1 may receive a result of processing a message from the peripheral device 2000 of FIG. 1 by setting a bit '7' of the "message flag" 404 to '1'.

Also, the host device 1000 may set a bit '6' and transmit a message to change or control settings of the peripheral device 2000.

The "invoke ID" 406 may be a value representing a request for information when the host device 1000 requests the peripheral device 2000 to provide the information, as will be described with reference to FIG. 6 below. When the host device 1000 requests the peripheral device 2000 to provide the information, the "invoke ID" 406 may have a value greater than '0'. Also, the peripheral device 2000 may respond to the request by using the "invoke ID" 406 used to request the information.

Also, as will be described with reference to FIG. 6 below, the "invoke ID" 406 may be '0' when the peripheral device 2000 transmits a message to the host device 1000 when a request for the message is not received from the host device 1000.

The "extended message ID" 408 is an ID of a message. The "extended message ID" 408 may be a common message ID when the "extended message ID" 408 has a value of "0x00" to "0x4F", and may be a private message ID when the "extended message ID" 408 has a value of "0x50" to "0x9F".

A health information message of the common message ID may be a message commonly applied to peripheral devices 2000. For example, a health information message having an "extended message ID" 408 of '0x00' (e.g., a data request message) may be interpreted to be the same by all the peripheral devices 2000 and the host device 1000.

A health information message having a private message ID may be interpreted differently in units of peripheral devices 2000. For example, when a health information message having an "extended message ID" 408 of '0x70' is used in relation to a pulse oximeter, the health information message may be interpreted as a message representing a pulse rate measured by the pulse oximeter. As another example, when the health information message having the "extended message ID" 408 of '0x70' is used in relation to a scale, the health information message may be interpreted as a message representing a weight measured by the weighing scale.

The "length" 410 represents the length of a message body 412.

The "message body" 412 represents health data to be exchanged between the host device 1000 and the peripheral device 2000. The structure of the "message body" 412 may depend on the "extended message ID". Reserved attributes may be present in "message body" regions in most messages.

FIG. 5 is a block diagram of a host device 1000 according to an exemplary embodiment.

As illustrated in FIG. 5, the host device 1000 according to an exemplary embodiment includes a message generating unit 1100 (e.g., second message generator), a message providing unit 1200 (e.g., second message provider), a message receiving unit 1300 (e.g., second message receiver), a second memory 1400, and a control unit 1500 (e.g., second controller).

The message generating unit 1100 generates a message to be transmitted to the peripheral device 2000. The message generating unit 1100 may generate a message requesting a health information message. Also, the message generating unit 1100 may generate, for example, a message requesting information regarding a raw data format, a message requesting real-time raw data, a message requesting a list of additional health data, and a message requesting additional health data.

The message providing unit 1200 transmits the generated message to the peripheral device 2000. The message receiving unit 1300 receives a health information message from the peripheral device 2000.

The memory 1400 stores data to be used by the host device 1000 to request, receive, and interpret the health information message.

The control unit 1500 extracts health data from the health information message received from the peripheral device 2000. The control unit 1500 may extract health data from the health information message by using a message ID of the health information message. For example, when the message ID of the health information message is a common message ID, the control unit 1500 may extract health data from the health information message and interpret the health data regardless of the type of the peripheral device 2000. For example, when the message ID of the health information message is a private message ID, the control unit 1500 may extract health data from the health information message and interpret the health data, based on a combination of an ID of the peripheral device 2000 and the private message ID.

At least one of the message generating unit 1100, the message providing unit 1200, the message receiving unit 1300, and the control unit 1500 may be operated by a software module, but are not limited thereto. Also, at least one of the message generating unit 1100, the message providing unit 1200, the message receiving unit 1300, the memory 1400 and the control unit 1500 may be operated by hardware.

At least one of the message generating unit 1100, the message providing unit 1200, and the message receiving unit 1300 may be included in the control unit 1500. At least one of the message generating unit 1100, the message providing unit 1200, the message receiving unit 1300, and the control unit 1500 may be operated by a processor, but are not limited thereto.

Figure 6:
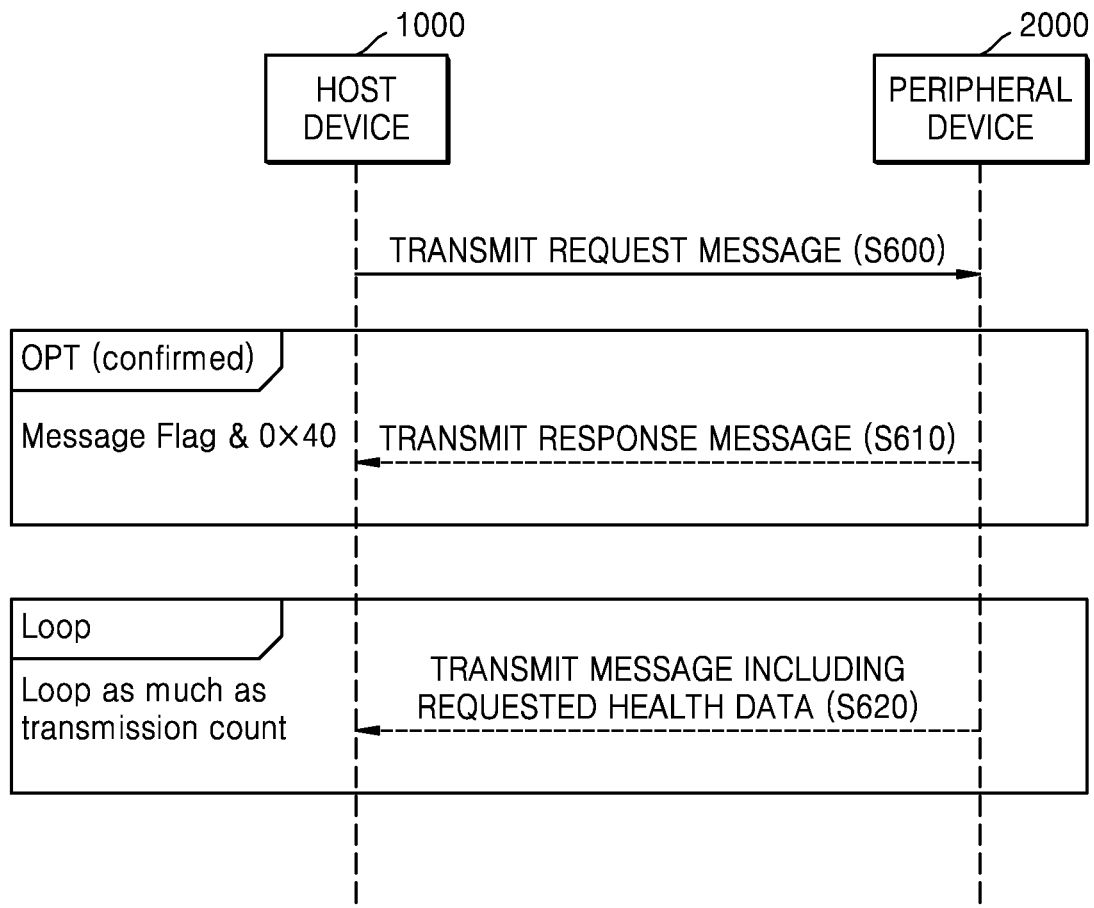
FIG. 6 is a diagram of a method of providing a health information message to a host device from a peripheral device, in response to a request from the host device, according to an exemplary embodiment.

FIG. 6 is a diagram of a method of providing a health information message to a host device 1000 from a peripheral device 2000, in response to a request from the host device 1000, according to an exemplary embodiment.

In operation S600, the host device 1000 transmits a request message requesting health data to the peripheral device 2000. In operation S610, the peripheral device 2000 transmits a response message indicating the receipt of the request message to the host device 1000. In operation S610, the peripheral device 2000 may inform the host device 1000 that the health data requested by the host device 1000 may be provided to the host device 1000.

In operation S620, the peripheral device 2000 transmits a message including the requested health data to the host device 1000. The peripheral device 2000 may identify the type of the requested health data from the requested message received from the host device 1000, generate the health data, and include the health data in a message to be provided to the host device 1000. Also, the peripheral device 2000 may determine a message ID of the message, which is to be provided to the host device 1000, to be a common message ID or a private message ID, based on the type of the health data.

Figure 7:
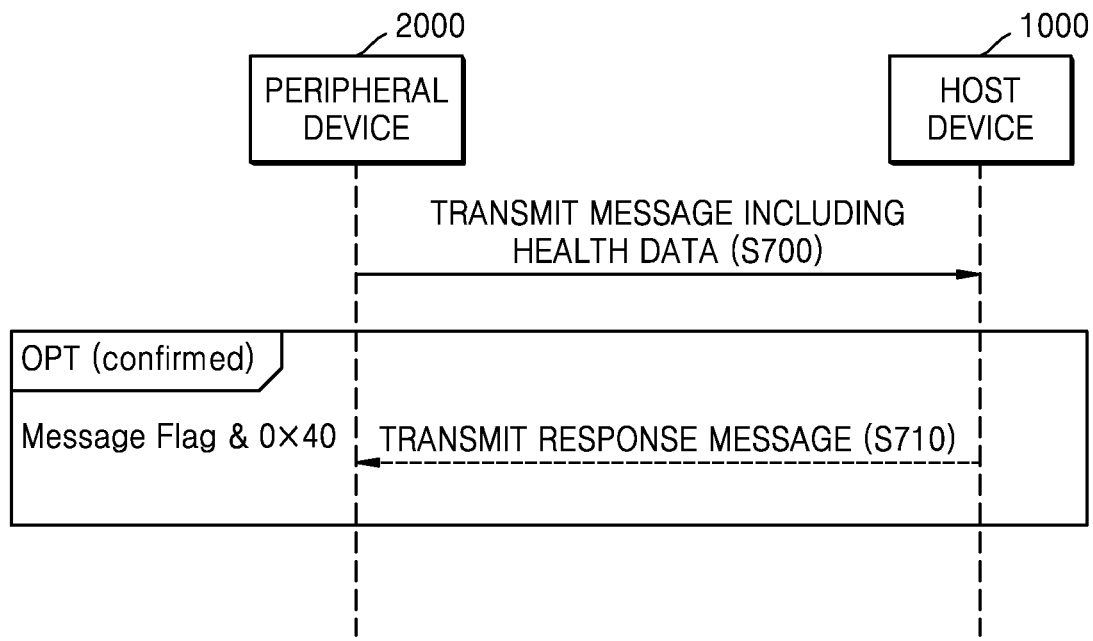
FIG. 7 is a diagram of a method of providing a health information message to a host device from a peripheral device when a request for the health information message is not received from the host device, according to another exemplary embodiment.

FIG. 7 is a diagram of a method of providing a health information message to a host device 1000 from a peripheral device 2000 when a request for the health information message is not received from the host device 1000, according to another exemplary embodiment.

In operation S700, the peripheral device 2000 transmits a message including health data to the host device 1000 even though a request for the predetermined health data has not been received by the peripheral device 2000 from the host device 1000. The health data may be data representing the state of the peripheral device 2000, and may include, for example, alarm information, notice information, and event information related to the state of the peripheral device 2000. The alarm information may include information indicating, for example, the occurrence of an error, a low battery level, separation of an adapter, etc. The notice information may include information indicating, for example, that a battery has reached a full charge level, a connection to an adapter, an operating temperature, etc. The event information may be information related to, for example, the occurrence of arrhythmia, tachycardia, or bradycardia, but is not limited thereto.

The peripheral device 2000 may determine a message ID of the message, which is to be provided to the host device 1000, to be a common message ID or a private message ID, based on the type of the health data. The message to be provided to the host device 1000 may include, for example, alarm information, notice information, and event information.

In operation S710, the host device 1000 may transmit a response message indicating the receipt of the message from the peripheral device 2000 to the peripheral device 2000.

Figure 8:
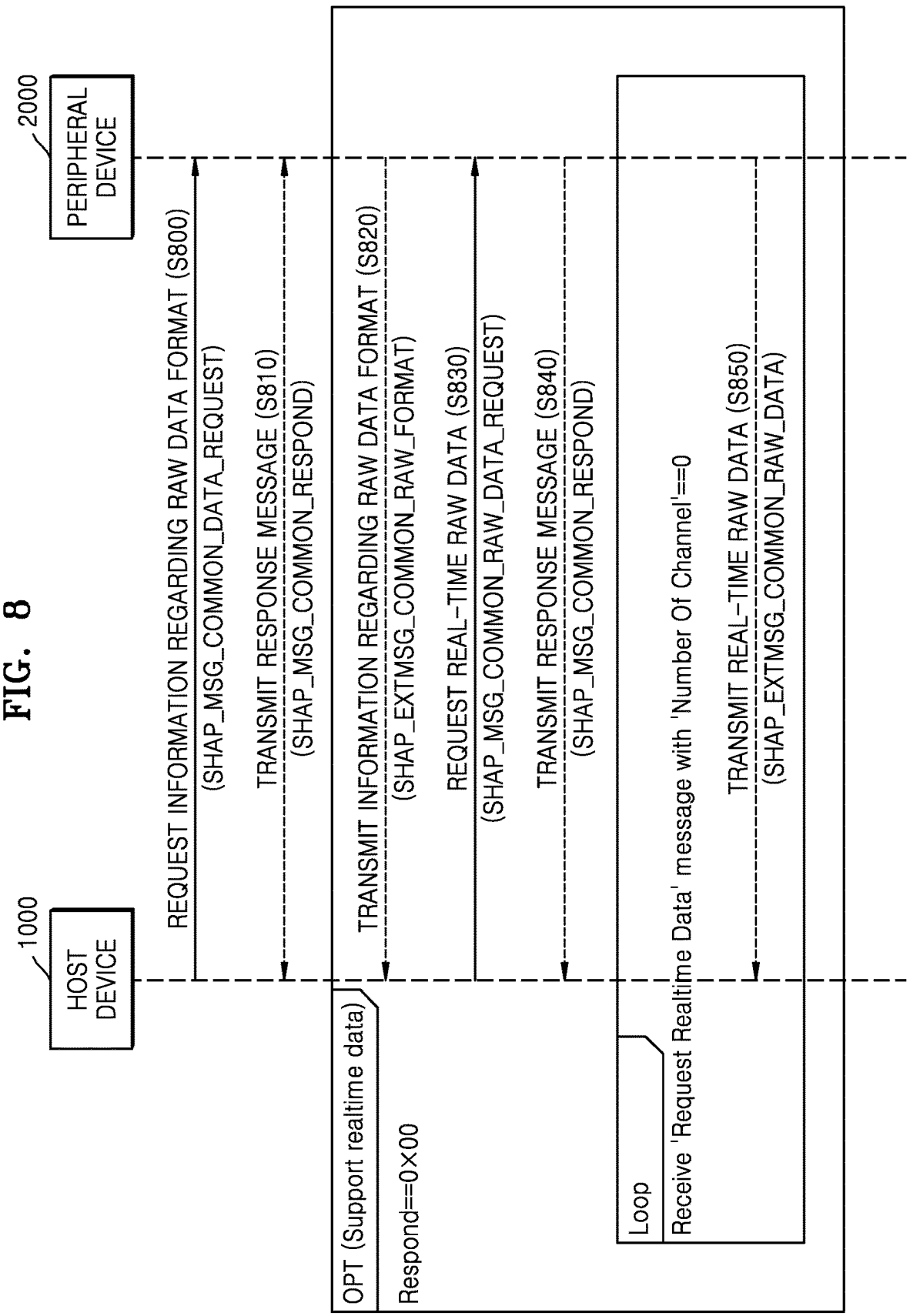
FIG. 8 is a diagram of a method of providing raw data, which is generated by a peripheral device, to a host device from the peripheral device in real time, according to an exemplary embodiment.

FIG. 8 is a diagram of a method of providing raw data, which is generated by a peripheral device 2000, to a host device 1000 from the peripheral device 2000 in real time, according to an exemplary embodiment.

The raw data is measured and generated by the peripheral device 2000, and may include, for example, generic waveform data, electrocardiogram data, electroencephalogram data, electrooculogram data, electromyogram data, blood pressure data, data related to a galvanic skin response (GSR), plethysmogram data, blood flow data, and temperature data.

In operation S800, the host device 1000 requests the peripheral device 2000 to provide information regarding a raw data format. In operation S810, the peripheral device 2000 may transmit a response message to the host device 1000 so as to inform the host device 1000 that the information regarding the raw data format may be provided to the host device 1000.

In operation S820, the peripheral device 2000 transmits the information regarding the raw data format to the host device 1000. The information regarding the raw data format may include, for example, information regarding the type of the raw data, sample size, sampling frequency, a unit of the raw data, and a channel of the raw data (e.g., a channel ID and the number of channels).

In operation S830, the host device 1000 requests the peripheral device 2000 to provide real-time raw data. According to an exemplary embodiment, the real-time raw data is raw data generated by the peripheral device 2000 in real time. The host device 1000 may provide the peripheral device 2000 with information regarding a channel via which the real-time raw data is to be transmitted while requesting the peripheral device 2000 to provide the real-time raw data.

In operation S840, the peripheral device 2000 transmits a response message to the host device 1000 so as to inform the host device 1000 that the real-time raw data requested by the host device 1000 may be provided to the host device 1000.

In operation S850, the peripheral device 2000 transmits the real-time raw data to the host device 1000. The peripheral device 2000 may transmit the real-time raw data to the host device 1000 a predetermined number of times.

Figure 9A:
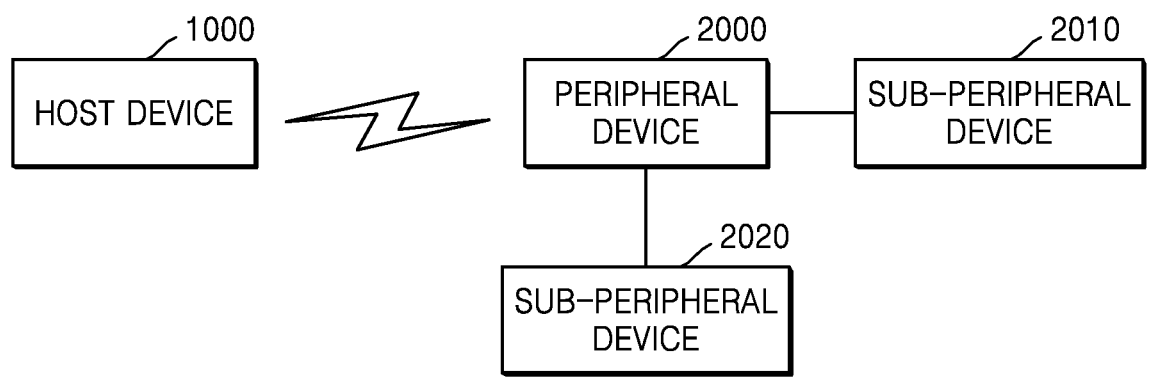
FIGS. 9A and 9B are block diagrams illustrating connections between a peripheral device and sub-peripheral devices, according to an exemplary embodiment.
Figure 9B:
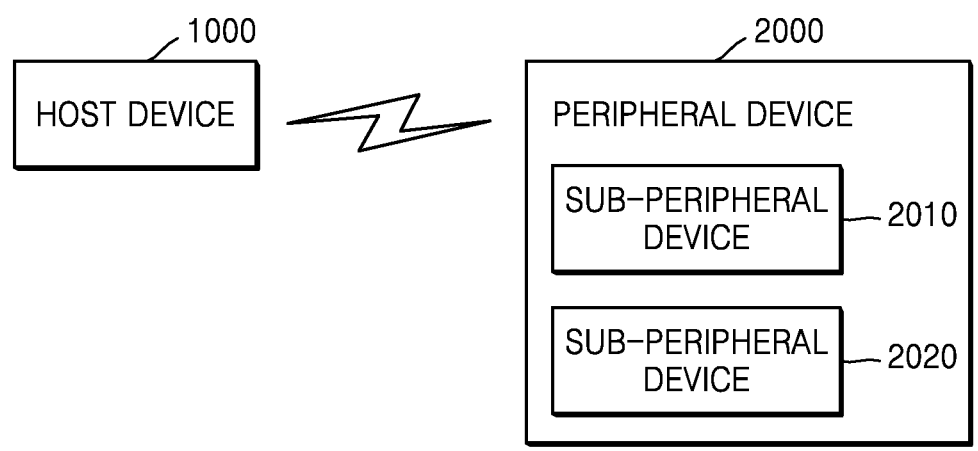

FIGS. 9A and 9B are block diagrams illustrating connections between a peripheral device 2000 and sub-peripheral devices 2010 and 2020, according to an exemplary embodiment.

Referring to FIG. 9A, the sub-peripheral devices 2010 and 2020 may be external devices connected to and external from the peripheral device 2000. Referring to FIG. 9B, the sub-peripheral devices 2010 and 2020 may be included in the peripheral device 2000.

The peripheral device 2000 may provide the host device 1000 with a list of the sub-peripheral devices 2010 and 2020 and a list of the health data generated by the sub-peripheral devices 2010 and 2020. Also, the peripheral device 2000 may provide health data generated by the sub-peripheral devices 2010 and 2020 to the host device 1000.

Figure 10:
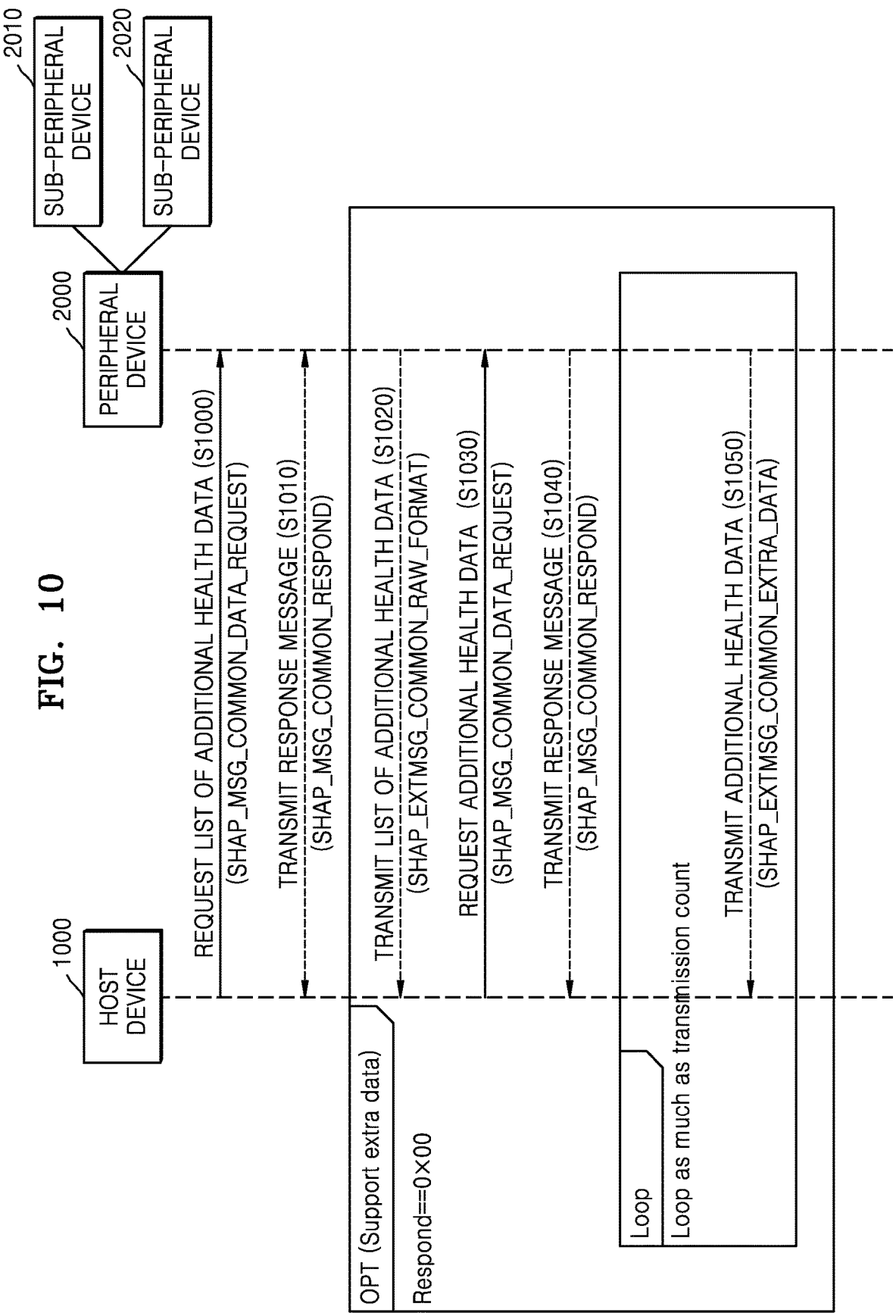
FIG. 10 is a diagram of a method of providing health information data, which is generated by sub-peripheral devices, to a host device from a peripheral device, according to an exemplary embodiment.

FIG. 10 is a diagram of a method of providing health information data, which is generated by sub-peripheral devices 2010 and 2020, to a host device 1000 from a peripheral device 2000, according to an exemplary embodiment.

In operation S1000, the host device 1000 requests the peripheral device 2000 to provide a list of additional health data. The additional health data is understood as health data generated by the sub-peripheral devices 2010 and 2020 connected to the peripheral device 2000, and provided from the peripheral device 2000 to the host device 1000.

In operation S1010, the peripheral device 2000 transmits a response message to the host device 1000 so as to inform the host device 1000 that the list of additional health data requested by the host device 1000 may be provided to the host device 1000.

In operation S1020, the peripheral device 2000 transmits the list of additional health data to the host device 1000. The peripheral device 2000 may transmit a list of the sub-peripheral devices 2010 and 2020 connected thereto and a list of health data generated by the sub-peripheral devices 2010 and 2020 to the host device 1000.

In operation S1030, the host device 1000 requests the peripheral device 2000 to provide additional health data. The host device 1000 may select health data from the list of additional health data received from the peripheral device 2000. Also, the host device 1000 may request the peripheral device 2000 to provide the selected health data.

In operation S1040, the peripheral device 2000 transmits a response message to the host device 1000 so as to inform the host device 1000 that the additional health data requested by the host device 1000 may be provided to the host device 1000.

In operation S1050, the peripheral device 2000 transmits additional health data generated by the sub-peripheral devices 2010 and 2020 to the host device 1000. The peripheral device 2000 may receive the additional health data requested by the host device 1000 from the sub-peripheral devices 1010 and 1020, and transmit a message including the additional health data to the host device 1000. In this case, the message including the additional health data may include a message ID and IDs of the sub-peripheral devices 2010 and 2020 that generate the additional health data. Also, the peripheral device 2000 may transmit the additional health data to the host device 1000 a predetermined number of times.

Thus, the host device 1000 may identify the type of the additional health data and extract the additional health data from the message, based on the message ID of the message including the additional health data and the IDs of the sub-peripheral devices 2010 and 2020. In particular, when the message ID of the message including the additional health data is a private message ID, the host device 1000 may use the IDs of the sub-peripheral devices 2010 and 2020 to extract the additional health data from the message.

Certain exemplary embodiments may be embodied as a non-transitory computer-readable recording medium that stores commands that are executable by a computer, e.g., program modules that are executed by a computer. The non-transitory computer-readable recording medium may be a medium that is accessible by a computer, and may be, for example, a volatile or non-volatile medium, a separable or non-separable medium, etc. Also, the non-transitory computer-readable recording medium may include both a computer storage medium and a communication medium. Examples of the computer storage medium include a volatile or non-volatile medium, a separable or non-separable medium, etc., which are configured to store information such as computer-readable commands, data structures, program modules, or other data according to an arbitrary method or technique. Typical examples of the communication medium include a transmission mechanism that transmits computer-readable commands, data structures, program modules, or other data of a modulated data signal or any of various types of information transmission media.

It should be understood that the exemplary embodiments described therein should be considered in a descriptive sense only and not for purposes of limitation. Descriptions of features or aspects within each exemplary embodiment should typically be considered as available for other similar features or aspects in other exemplary embodiments. For example, components described as being combined in a single form may be embodied as being dispersed. Similarly, components described as being dispersed may be embodied as being combined in a single form.

The scope of certain exemplary embodiments is defined in the claims appended herein rather than the detailed description, and the above exemplary embodiments should be understood as covering all modifications, equivalents, and alternatives falling within the scope of the certain exemplary embodiments.

While one or more exemplary embodiments have been described with reference to the figures, it will be understood by those of ordinary skill in the art that various changes in form and details may be made therein without departing from the spirit and scope as defined by the following claims.

What is claimed is:

1. A medical device for providing a health information message to a host device, the medical device comprising:
    a health data obtainer configured to obtain health data;
    a message generator configured to determine a type of the health data, a private message identification (ID) corresponding to the type of the health data, and an ID of the medical device, and generate the health information message, the health information message including the private message ID, the ID of the medical device, and the health data; and
    a message provider configured to transmit the health information message in a message format to the host device,
    wherein the private message ID is configured to be interpreted differently according to the ID of the medical device,
    wherein the message format comprises one of:
        a standard message format configured to be used to transmit health data generated by the medical device; and
        an extended message format configured to be used when message providers of a plurality of medical devices transmit a plurality of health data each of which is obtained by a respective medical device of the plurality of medical devices, when the message provider transmits health data variably generated by the medical device, or when a number of types of the health data is greater than a predetermined level, and
    wherein the message format is selected from one of the standard message format and the extended message format based on the type of the health data.

2. The medical device of claim 1, wherein the message generator is further configured to generate a message ID of the health information message, the message ID being classified as one of the private message ID and a common message ID.

3. The medical device of claim 2, wherein the message ID is expressed in a predetermined number of bits,
    wherein some values expressed in the predetermined number of bits indicate the private message ID, and
    other values expressed in the predetermined number of bits indicate the common message ID.

4. The medical device of claim 1, wherein the health data comprises raw data, and the medical device further comprises a sensor configured to measure the raw data in real time.

5. The medical device of claim 1, wherein the health data obtainer is configured to obtain health data generated by sub-medical devices connected to the medical device, and
    wherein the message generator is configured to generate a health information message to include the health data generated by the sub-medical devices and IDs of the sub-medical devices.

6. The medical device of claim 5, wherein the health information message including the health data generated by the sub-medical devices and the IDs of the sub-medical devices comprises the private message ID, and
    the health data generated by the sub-medical devices is configured to be extracted by the host device, based on the private message ID and the IDs of the sub-medical devices.

7. The medical device of claim 5, further comprising a message receiver configured to receive a request for additional health data from the host device,
    wherein the message generator is configured to generate a health information message to include the health data generated by the sub-medical devices and the IDs of the sub-medical devices, in response to the request for the additional health data.

8. The medical device of claim 7, wherein the medical device is configured to transmit a list of the sub-medical devices and a list of the health data generated by the sub-medical devices to the host device, in response to the request for the additional health data.

9. The medical device of claim 5, wherein the sub-medical devices are included in the medical device.

10. A method of providing a health information message from a medical device to a host device, the method comprising:
    obtaining health data;
    determining a type of the health data, a private message identification (ID) corresponding to the type of the health data, and an ID of the medical device;
    generating the health information message to include the private message ID, the ID of the medical device, and the health data; and
    transmitting the health information message in a message format to the host device, wherein the private message ID is configured to be interpreted differently according to the ID of the medical device, wherein the message format comprises one of:
    a standard message format configured to be used to transmit health data generated by the medical device; and
    an extended message format configured to be used when a plurality of medical devices transmit a plurality of health data, each of which is obtained by a respective medical device of the plurality of medical devices, when health data variably generated by the medical device is transmitted, or when a number of types of the health data is greater than a predetermined level, and
    wherein the message format is selected from one of the standard message format and the extended message format based on the type of the health data.

11. The method of claim 10, further comprising classifying a message ID of the health information message as one of the private message ID and a common message ID.

12. The method of claim 11, wherein the message ID is expressed in a predetermined number of bits,
    wherein some values expressed in the predetermined number of bits indicate the private message ID, and
    other values expressed in the predetermined number of bits are set to the common message ID.

13. The method of claim 10, wherein the health data comprises raw data, and the method further comprises measuring the raw data in real time using a sensor of the medical device.

14. The method of claim 10, wherein the obtaining comprises obtaining health data generated by sub-medical devices connected to the medical device, and
    the generating of the health information message comprises generating the health information message to include the health data generated by the sub-medical devices and IDs of the sub-medical devices.

15. The method of claim 14, wherein the health information message including the health data generated by the sub-medical devices and the IDs of the sub-medical devices comprises the private message ID, and
    the health data generated by the sub-medical devices is configured to be extracted by the host device, based on the private message ID and the IDs of the sub-medical devices.

16. The method of claim 14, further comprising receiving a request for additional health data from the host device, and
    wherein the generating of the health information message comprises generating the health information message to include the health data generated by the sub-medical devices and the IDs of the sub-medical devices, in response to the request for the additional health data.

17. The method of claim 16, further comprising transmitting a list of the sub-medical devices and a list of the health data generated by the sub-medical devices to the host device, in response to the request for the additional health data.

18. The method of claim 14, wherein the sub-medical devices are included in the medical device.

19. A non-transitory computer-readable recording medium having recorded thereon a program including commands which, when executed, cause a computer to perform a method of providing a health information message from a medical device to a host device, the method comprising:
    obtaining health data;
    determining a type of the health data, a private message identification (ID) corresponding to the type of the health data, and an ID of the medical device;
    generating the health information message to include the private message ID, the ID of the medical device, and the health data; and
    transmitting the health information message in a message format to the host device,
    wherein the private message ID is configured to be interpreted differently according to the ID of the medical device,
    wherein the message format comprises one of:
        a standard message format configured to be used to transmit health data generated by the medical device; and
        an extended message format, the extended message format being configured to be used when a plurality of medical devices transmit a plurality of health data each of which is obtained by a respective medical device of the plurality of medical devices, when health data variably generated by the medical device is transmitted, or when a number of types of the health data is greater than a predetermined level, and
        wherein the message format is selected from one of the standard message format and the extended message format based on the type of the health data.

20. A host device, comprising:
a message receiver configured to receive, from a medical device and in a message format, a message including health data, an ID of the medical device, and a private message ID corresponding to a type of the health data; and
a controller configured to determine the type of the health data according to the ID of the medical device and the private message ID, and process the health data according to the determined type,
wherein the private message ID is configured to be interpreted differently according to the ID of the medical device,
wherein the message format comprises one of:
    a standard message format configured to be used to transmit health data generated by the medical device; and
    an extended message format configured to be used when a plurality of medical devices transmit a plurality of health data each of which is obtained by a respective medical device of the plurality of medical devices, when the medical device transmits health data variably generated by the medical device, or when a number of types of the health data is greater than a predetermined level, and
    wherein the message format is selected from one of the standard message format and the extended message format based on the type of the health data.

21. The host device of claim 20, further comprising a message provider configured to transmit a request to the medical device requesting the message.

22. The host device of claim 20, wherein the host device comprises a mobile phone.

23. The medical device of claim 1,
wherein the message provider is configured to, in response to the health information message comprising the standard message format, transmit the health information message to the host device in the standard message format, and
wherein the message provider is configured to, in response to the health information message comprising the extended message format, transmit the health information message to the host device in the extended message format.

24. The method of claim 10,
wherein the transmitting the health information to the host device further comprises, in response to the health information message including the standard message format, transmitting the health information to the host device in the standard message format, and
wherein the transmitting the health information to the host device further comprises, in response to the health information message including the extended message format, transmitting the health information to the host device in the extended message format.

* * * * *